United States Patent [19]

VandenBerg

[11] Patent Number: Plant 7,435

[45] Date of Patent: Jan. 29, 1991

[54] CHRYSANTHEMUM PLANT NAMED PAPILLON

[75] Inventor: Cornelis P. VandenBerg, Salinas, Calif.

[73] Assignee: Yoder Brothers, Inc., Barberton, Ohio

[21] Appl. No.: 435,825

[22] Filed: Nov. 14, 1989

[51] Int. Cl.[5] ..... A01H 5/00
[52] U.S. Cl. ..... Plt./74
[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Papillon particularly characterized by its flat capitulum form; daisy capitulum type; red-purple ray floret color; diameter across face of capitulum of 35 to 37 mm at maturity when grown as a pinched spray pot mum; very floriferous habit, with an excellent display of many small flowers; uniform seven week photoperiodic flowering response to short days; medium plant height when grown as a pinched pot mum; small, dark green foliage; and its spreading and very prolific branching pattern.

3 Drawing Sheets

The present invention comprises a new and distinct cultivar of Chrysanthemum, botanically known as *Dendranthema grandiflora,* and referred to by the cultivar name Papillon.

Papillon, Identified as 86-72002, was originated from a cross made by Cornelis P. VandenBerg in a controlled breeding program in Salinas, Calif., in 1986.

The female parent of Papillon was an unnamed seedling identified as 82-276008. The male parent of Papillon was an unnamed seedling identified as 83-S07005.

Papillon was discovered and selected as one flowering plant within the progeny of the stated cross by Cornelis P. VandenBerg in January of 1987, in a controlled environment in Salinas, Calif.

The first act of asexual reproduction of Papillon was accomplished when vegetative cuttings were taken from the initial selection in March of 1987 in a controlled environment in Salinas, Calif, by technicians working under formulations established and supervised by Cornelis P. VandenBerg.

Horticultural examination of controlled flowerings of successive plantings has shown that the unique combination of characteristics as herein disclosed for Papillon are firmly fixed and are retained through successive generations of asexual reproduction.

Papillon has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Papillon, which, in combination, distinghish this Chrysanthenmum as a new and distinct cultivar:

1. Flat capitulum form.
2. Daisy capitulum type.
3. Red-purple ray floret color.
4. Diameter across face of capitulum of 35 to b 37 mm at maturity, when grown as a pinched spray pot mum.

5. Very floriferous, with an excellent display of many small flowers.
6. Uniform eight week photoperiodic flowering response to short days.
7. Medium plant height, requiring 0 to 7 long days after pinch prior to short days and 1 to 2 applications of 2500 ppm B-9 SP to attain a flowered plant height of 25 to 35 cm for year-round flowerings when grown as a pinched pot mum in a 15 cm pot.
8. Small, dark green foliage.
9. Branching pattern is spreading and very prolific, with each plant having 6 to 8 laterals after pinch.

The accompanying photographic drawings show typical inflorescence and leaf characteristics of Papillon, with the colors being as nearly true as possible with illustrations of this type. Sheet 1 is a color photograph of Papillon grown as a pinched spray pot mum in a 15 cm pot. Sheet 2 is a black and white photograph of three views of the inflorescence of Papillon. Sheet 3 is a black and white photograph showing the upper and under sides of the leaves of Papillon at three stages of development (mature, intermediate and immature).

No commercial cultivar known to the inverter can be compared with Papillon. The combination of red-purple flower color, very high number of small flowers, small dark green foliage, and its spreading and very prolific branching pattern is unique, and is not represented in any commercial cultivar known to the inventor.

In the following description color references are made to The Royal Horticultural Society Color Chart. The color values were determined on plant material grown as a pinched spray pot mum in Salinas, Calif. on June 5, 1989.

Classification:
*Botanical.*—*Dendranthema grandiflora* cv Papillon.
*Commercial.*—Daisy spray pot mum.

INFLORESCENCE

A. Capitulum:
*Form.*—Flat.
*Type.*—Daisy.

*Diameter across face.*—From 35 to 37 mm at maturity.

B. Corolla of ray florets:

*Color (general tonality from a distance of three meters).*—Red-purple.

*Color (upper surface).*—71B to 71C.

*Color (under surface).*—74C to 74D.

*Shape.*—Straight, oblong, slightly ribbed.

C. Corolla of disc florets:

*Color (mature).*—12A.

*Color (immature).*—3A with slight overcast of 144C.

D. Reproductive organs:

*Androecium.*—Present on disc florets only; moderate pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 to 2 applications of 2500 ppm B-9 SP, when grown as a pinched pot mum in a 15 cm pot.

*Branching pattern.*—Spreading and very prolific.

B. Foliage:

*Color (upper surface).*—147A.

*Color (under surface).*—147B.

*Shape.*—Small, lobed and slightly serrated.

I claim:

1. A new and distinct Chrysanthemum plant named Papillon, as described and illustrated.

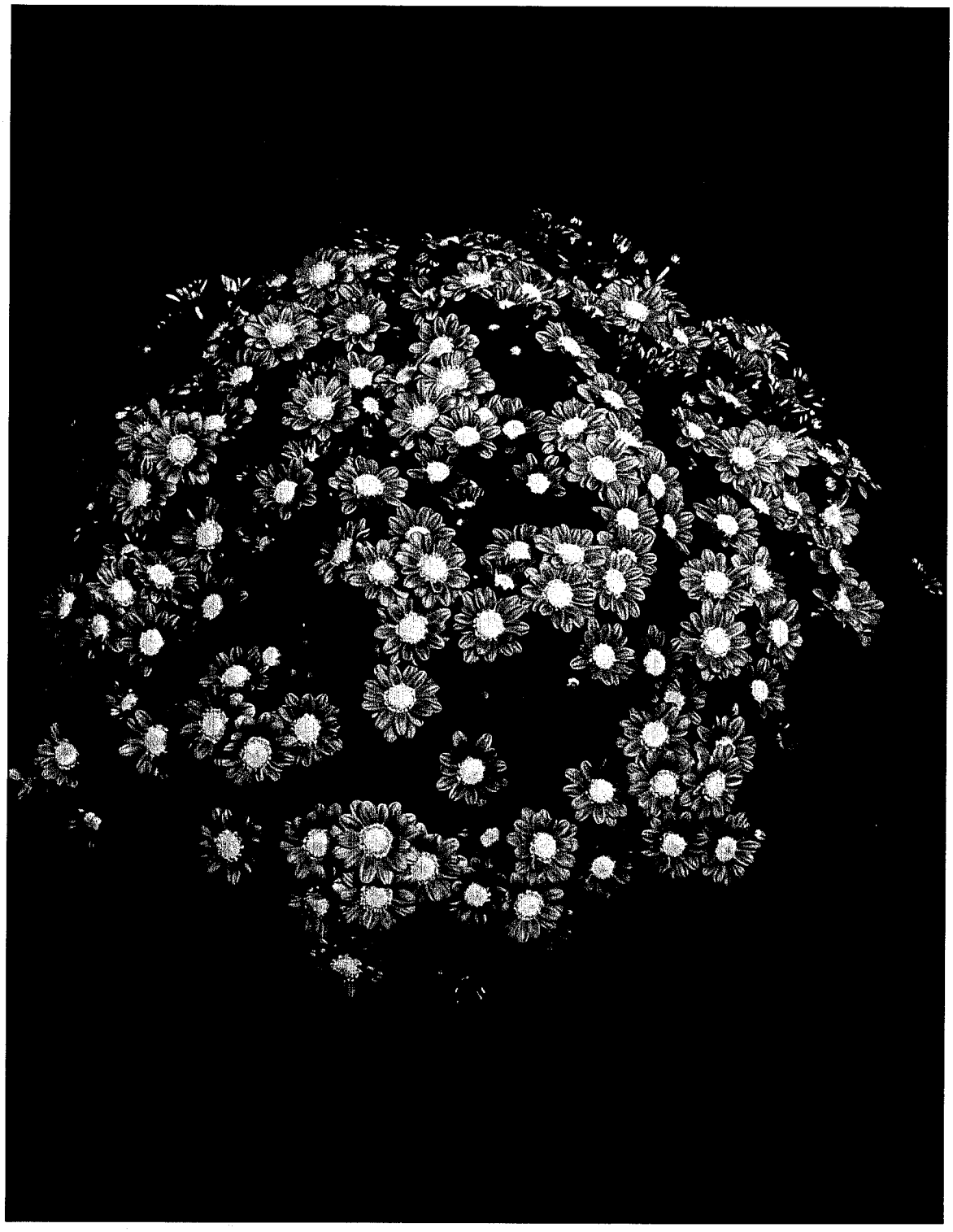

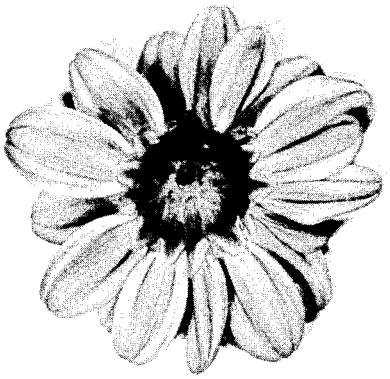
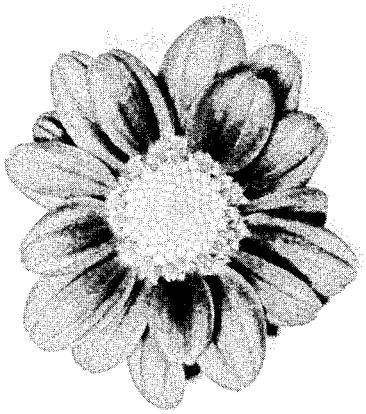
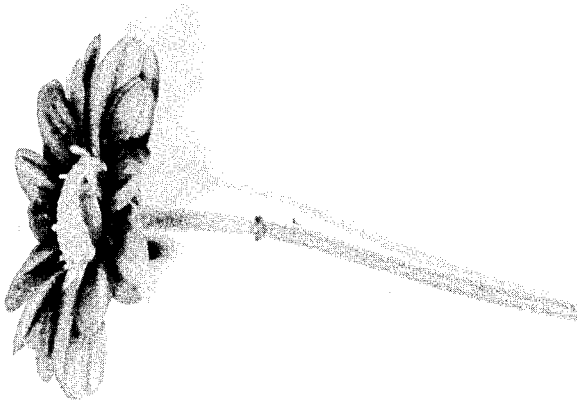

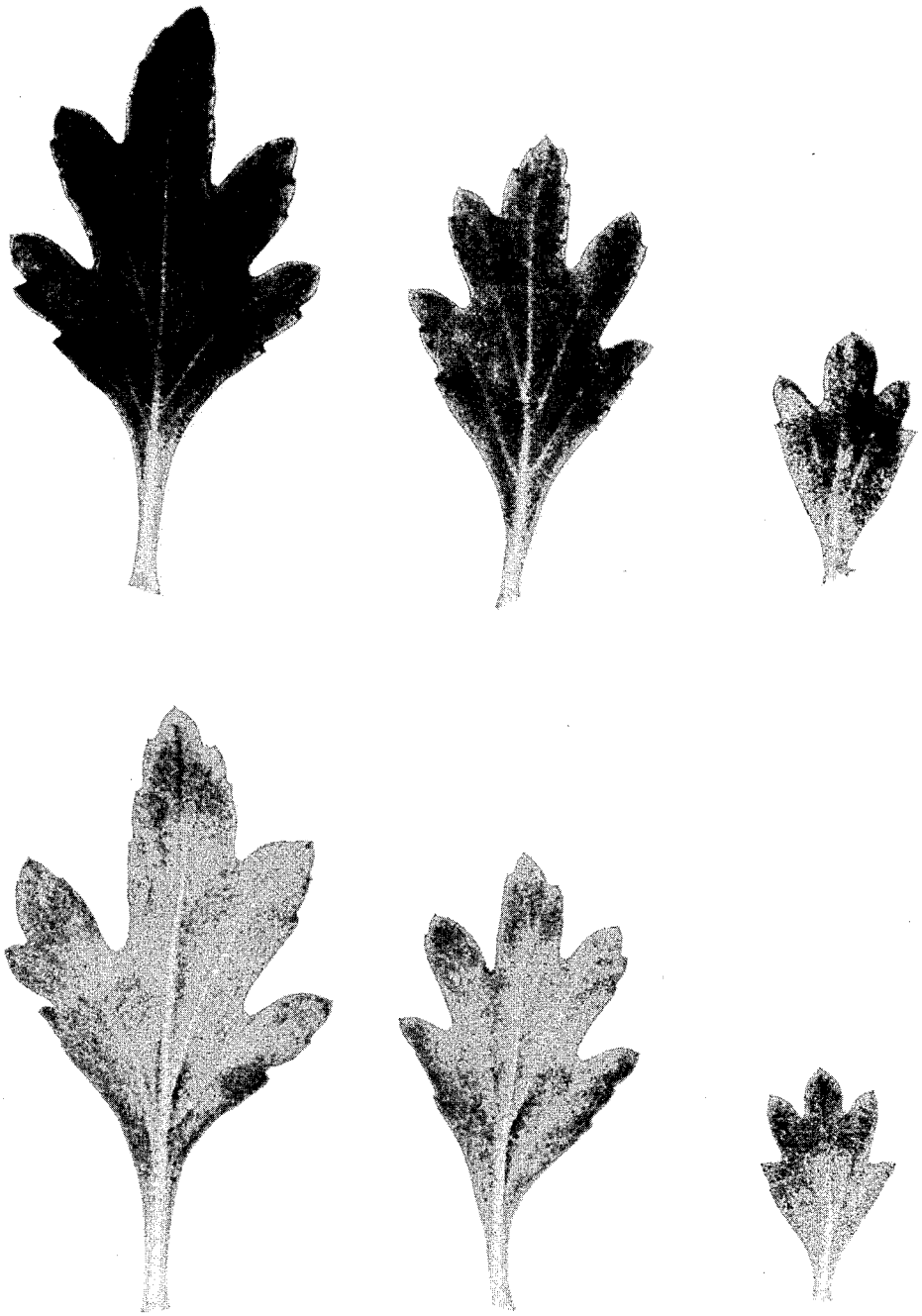

* * * * *